United States Patent [19]

Sakai et al.

[11] Patent Number: 4,760,096

[45] Date of Patent: Jul. 26, 1988

[54] MOISTURIZING SKIN PREPARATION

[75] Inventors: Kirk Sakai, Coral Springs; Timothy W. Quick, Pembroke Pines, both of Fla.

[73] Assignee: Schering Corporation, Kenilworth, N.J.

[21] Appl. No.: 781,061

[22] Filed: Sep. 27, 1985

[51] Int. Cl.$^4$ ................................................ A61K 7/48
[52] U.S. Cl. .................................. 514/847; 514/937; 514/938; 514/939; 514/944; 514/969
[58] Field of Search ............... 514/846, 847, 937, 939; 424/78, 167

[56] References Cited

U.S. PATENT DOCUMENTS 4,537,782  8/1985  Millet et al. ........................... 514/78

FOREIGN PATENT DOCUMENTS

| 100964 | 2/1984 | European Pat. Off. | ............ 514/844 |
| 209207 | 12/1982 | Japan | ..................... 424/59 |
| 0193812 | 11/1984 | Japan | ..................... 514/78 |
| 2050799 | 1/1981 | United Kingdom | ................... 514/78 |

OTHER PUBLICATIONS

Rabinowitz et al, Chem. Abs., 1972, vol. 76, p. 150262v.
Oreal, Chem. Abs., 1984, p. 12453w, vol. 100.
Kooyman, D. J., "LXI—Lipids of the Skin: Some Changes in the Lipids of the Epidermis During the Process of Keratirization", Arch. Dermat & Syph. 25:444 (1932).
C.A. 98:95488a, vol. 98, p. 362, Cosmetic Creams and Emulsions, Abstract of JP 57, 209, 207, Jun. 17, 1981.
Ogiwara et al., C.A. 126,692t, vol. 81, p. 417.

*Primary Examiner*—Dale R. Ore
*Attorney, Agent, or Firm*—James R. Nelson; Gerald S. Rosen; Stephen I. Miller

[57] ABSTRACT

A skin moisturizing preparation, such as a skin cream, face cream, lotion or ointment containing a combination of a phosphatide such as soy lecithin and one or more $C_{10}$–$C_{30}$ carboxylic acid sterol esters. The preparation preferably also contains a caprylic/capric acid triglyceride for enhanced moisturization. There is also described a method of treating dry skin by topical application of such moisturizing preparations.

16 Claims, No Drawings

MOISTURIZING SKIN PREPARATION

FIELD OF THE INVENTION

The present invention relates to a skin preparation comprising a combination of a phosphatide such as phosphatidylcholine (lecithin) and one or more $C_{10}$–$C_{30}$ carboxylic acid sterol esters, and more particularly to such a skin preparation which provides a combination of improved physiological effects, including skin softening, increased flexibility and moisturization. In a preferred embodiment of the present invention, the skin preparation further comprises one or more $C_6$–$C_{12}$ alkanoic triglycerides, such as caprylic or capric triglyceride.

BACKGROUND OF THE INVENTION

Epidermal basal cells have a complex lipid composition, characterized by cells containing different subcellular organells. During keratinization, the lipid composition (phosphatidylcholine, triacylglycerol, sterol, sterol ester, fatty acid) changes dramatically. Kooyman (Arch. Derm. Syph., 25, 444, 1932) and Long (J. Invest. Dermatol., 54, 174, 1970) compared the lipid composition of viable epidermis with stratum corneum and observed a striking decrease in the amount of phosphatidylcholine in the latter, indicating that phosphatidylcholine is present in high concentrations at the active sites of the epidermal metabolism. Concomitantly, this decrease in phosphatidylcholine is accompanied by an increase in the concentration of triacylglycerol and fatty acid.

In the stratum corneum, where keratinization comes to completion, a well-regulated balance of the phosphatidylcholine/sterol ratio exists, and this ratio is considered as very important for the maintenance of the physiological colloidal state of the cell protoplasm. Indeed, the disturbance of this relationship definitely contributes to the process of keratinization of stratum corneum which is replenished approximately every two weeks in a mature adult. It is also well known that the softness and flexibility of stratum corneum depends partially on the moisture content of the intercellular channels in this layer. Thus it has been long sought to find ways of restoring these vital qualities of the skin when they are lost, as occurs with the natural aging process, and in cases of extreme dryness.

In Canadian Pat. No. 1,134,276 it was disclosed that phosphatidylcholine, beside playing important physiological and biochemical roles, can form a complex which binds water and thereby creates a moisture reservoir which can restore a natural moisture balance to skin.

For skin preparations, numerous compositions have been proposed based on phosphatidylcholine (commonly called lecithin). Grate, U.S. Pat. No. 3,062,721, discusses lecithin in combination with certain other ingredients, which is said to provide a synergistic effect. He further explains that lecithin is a "skin's food" which penetrates deeply so as to facilitate the penetration of various other ingredients in the composition associated with the lecithin. Oleniacz, U.S. Pat. No. 3,957,971, discloses a liposome comprising a matrix of ternary lipid mixtures of lecithin, dicetylphosphate, and a sterol. Japanese Pat. No. JP 57/209207 (1982), discusses various uses contemplated for lecithin, cholesterol, and a combination of lecithin and cholesterol with acrylic polymers to promote deeper penetration of other ingredients into the epidermis.

A combination of phosphatidylcholine and sterol has been discussed for the treatment of infections, coughs, and respiratory diseases in Reifenrath, European Pat. No. EP100964.

SUMMARY OF THE INVENTION

In accordance with the present invention, it has been found that a skin preparation comprising a combination of a phosphatide such as phosphatidylcholine (lecithin) and one or more $C_{10}$–$C_{30}$ carboxylic acid sterol esters provides the skin with a combination of improved physiological effects, including moisturization, softening and increased flexibility. Such skin preparations include creams, lotions, face creams and ointments for topical application.

In a preferred embodiment of the present invention, the skin preparation further comprises one or more $C_6$–$C_{12}$ alkanoic triglycerides, such as caprylic or capric triglycerides.

It is therefore an object of the present invention to provide a skin preparation comprising a combination of a phosphatide and one or more $C_{10}$–$C_{30}$ carboxylic acid sterol esters.

It is a further object of the present invention to provide such a skin preparation in which the phosphatide is phosphatidylcholine.

A still further object of the present invention is to provide such a skin preparation which further comprises one or more $C_6$–$C_{12}$ alkanoic triglycerides such as caprylic or capric triglycerides.

A further object is to provide such preparations in the form of skin creams, lotions, ointments or face creams for topical application.

A still further object of the present invention is to provide a method of treating a dry skin condition by topically applying a skin preparation as disclosed herein.

DETAILED DESCRIPTION OF THE INVENTION

The present invention provides a skin preparation based upon the discovery that the combination of a phosphatide and one or more $C_{10}$–$C_{30}$ carboxylic acid sterol esters is particularly suitable for maintaining a healthy skin condition while providing a desirable moisture balance. The phosphatide and sterol esters are preferably provided in equimolar amounts because it is believed that the phosphatide molecules combine with the sterol ester molecules to form molecular complexes which provide the combination of improved physiological effects of the present invention.

A preferred phosphatide for use in the present invention is phosphatidylcholine, also known as lecithin. Lecithin is described in *The Merck Index* (Tenth Edition 1983) as a mixture of the diglycerides of stearic, palmitic, and oleic acids linked to the choline ester of phosphoric acid. It is therefore to be understood that any reference herein to lecithin or phosphatidylcholine is intended to include any combination of lecithin-like phosphatide compounds as is well known in the art. Examples of other phosphatides which can be used in accordance with the present invention include phosphatidylethanolamine (cephalin), phosphatidylserine, phosphatidylinositol, and phosphatidic acid. A mixture of these phosphatides can also be used.

It is advantageous to use commercially available lecithin-containing phosphatide mixtures as the source of phosphatide for the present invention, and soy phosphatide (soy lecithin) and egg phosphatide (egg lecithin) are particularly suitable. Such commercially available phosphatides contain various phosphatides and other components. While soy phosphatide is a mixture, it is considered to have an average molecular weight of about 750.

The amount of phosphatide used in the skin preparations of this invention varies with the condition or symptom to be treated and the formulation. Most commercially available phosphatides are mixtures of phosphatides with other components, and may vary from less than 5% active phosphatide to over 95% or even 100% actual phosphatide. The percent composition ranges herein are therefore based on 100% phosphatide, although the actual amount used in a composition would depend on its purity.

In the present invention, the amount of the phosphatide is normally in the range of about 0.05 to about 5 percent by weight, and preferably about 0.1 to about 1 percent by weight. If the phosphatide is used in too small amounts, the beneficial effects of this invention will not be attained sufficiently. When the phosphatide is used in an excessive amount, the effect of the skin preparation attained is not proportional to the amount of the phosphatide used, because the skin cannot absorb the excess phosphatide. In addition, the use of excessive phosphatide causes stickiness.

The skin preparations of the present invention also comprise one or more $C_{10}$–$C_{30}$ carboxylic acid sterol esters, also designated herein simply as sterol esters (SE). A preferred sterol ester for use in the present invention is "Super Sterol Ester" manufactured by Croda, Inc. which they describe as "$C_{10}$–$C_{30}$ carboxylic acid esters of sterols (predominantly cholesterol/lanosterol)". It is derived from wool wax by a process which is in part set forth in Koresawa et al, U.S. Pat. No. 4,138,416, which is incorporated herein by reference.

The sterol ester is preferably provided in equimolar proportion to the amount of phosphatide in the skin preparation of the present invention. In the case of phosphatidylcholine and Croda Super Sterol Ester, an equimolar composition is provided by a weight ratio of about 2 parts sterol ester to 3 parts phosphatidylcholine (on 100% purity basis).

More generally, as little as about 1 part sterol ester or as much as about 3 parts sterol ester may be used per 3 parts phosphatide by weight. Depending on the amount of phosphatide used, the amount of sterol ester used in a skin preparation in accordance with the present invention should be about 0.02 to about 5 percent by weight. Preferably, the skin preparation contains about 0.05 to about 1 percent by weight of the sterol ester.

The skin preparation of the present invention preferably also contains one or more alkanoic triglycerides. Well known, commercially available caprylic ($C_8$) and capric ($C_{10}$) triglyceride products are particularly suitable. A preferred alkanoic triglyceride material for use in the present invention is a caprylic/capric mixed acid triglyceride manufactured by Dynamit Nobel Corp. under the name Miglyol ®812 Neutral Oil. The manufacturers literature describes this neutral oil as having a fatty acid composition of 2% maximum caproic acid ($C_6$), 50–65% caprylic acid ($C_8$), 30–45% capric acid ($C_{10}$) and 3% maximum lauric acid ($C_{12}$).

A skin preparation in accordance with the present invention preferably contains about 0.5 to about 10 percent by weight, and more preferably about 2 to about 4 percent by weight, $C_6$–$C_{12}$ alkanoic triglyceride. In another composition of the present invention, a $C_6$–$C_{12}$ alkanoic triglyceride neutral oil is used as the base liquid to which the phosphatide and sterol ester are added.

The skin preparation of the present invention may be in the form of a skin cream, face cream, lotion, ointment, or any other suitable topical skin formulation. Depending upon the intended use of the skin preparation, other components can be incorporated into it to prepare a skin preparation having desired rheological properties.

Such formulations can be in the form of an aqueous mixture such as a solution, colloidal solution, emulsified lotion, oil-in-water cream (hydrophilic cream) or aqueous gel wherein the aqueous phase is the continuous one.

Alternatively, the formulation can be in the form of an oily mixture such as a solution, ointment, water-in-oil cream, gel base, absorption base or hydrophilic ointment wherein the oil phase is the continuous one. Such water-in-oil formulations are especially useful in preventing transdermal water loss and serve as effective carriers for transdermal drug delivery. Also, a non-aqueous water-soluble base such as a mixture with polyethylene glycol may be used.

A suspension base such as a shaking lotion, in which a solid dispersing agent is added, can also be prepared. Oily components, emulsifiers, dispersing agents, gelatinizers and solid materials which can be used to prepare such formulations are well known for use in the preparation of cosmetics and topical products.

The oily components include hydrocarbons such as liquid paraffin, petrolatum, solid paraffin, microcrystalline wax and the like; higher aliphatic alcohols such as cetyl alcohol, hexadecyl alcohol, stearyl alcohol, oleyl alcohol and the like, esters of higher aliphatic alcohols such as bees wax, spermaceti and the like; esters of higher aliphatic acids with lower alcohols such as isopropyl myristate, isopropyl palmitate and the like; vegetable oils and modified vegetable oils; anhydrous lanolin and its derivatives; squalene, squalane and the like; and higher aliphatic acids such as palmitic acid, stearic acid and the like.

Useful emulsifiers and dispersing agents include anionic, cationic and nonionic surfactants. Nonionic surfactants are preferred because of their low level of irritation to skin. Typical of nonionic surfactants are monoglycerides such as glyceryl monostearate and the like; sorbitan aliphatic esters such as sorbitan monolaurate and the like; sucrose aliphatic esters; polyoxyethylene aliphatic esters such as polyoxyethylene stearate; and polyoxyethylene higher alcohol ethers such as polyoxyethylene cetyl ether, polyoxyethylene oleyl ether, polyoxyethylene fatty ethers and the like.

Gelatinizers include carboxymethylcellulose, cellulose gel, Carbopol ® (carboxypolymethylene), polyvinyl alcohol, polyethylene glycol and various gums.

These oily components, emulsifiers, dispersing agents and gelatinizers can be used alone or in combination with each other.

The incorporation into the skin preparation of this invention of propylene glycol, glycerine, sorbitol or the like which have moisturizing action is preferred, because it enhances moisturizing action.

Ethanol may be provided as a component of the skin composition, ethanol having bacteriostatic action and providing a cooling effect upon application to the skin.

In order to increase the stability of the skin preparation of this invention, it is preferred to add antioxidants, chelating agents, preservatives and the like, if necessary. The antioxidants include butylated hydroxytoluene, butylated hydroxyanisole, tocopherol, sodium pyrosulfite, acetone sodium bisulfate and the like. The chelating agents include ethylenediaminetetraacetic acid (EDTA) and its derivatives, thioglycolic acid, thiolactic acid, thioglycerol and the like.

Suitable preservatives include diazolidinyl urea or imidazolidinyl urea as well as methyl, ethyl, propyl and butyl esters of p-hydroxybenzoic acid (parabens). Isothiazolones, such as those manufactured under the name Kathon®, may also be used.

In addition, it is preferred to adjust the pH of the skin preparation of this invention by adding citric acid, lactic acid, tartaric acid or the like. The desired final pH value is dependent upon the stability of the particular skin preparation. In general, it is preferred that the skin preparation be slightly acidic to slightly alkaline.

A fragrance may be added in a slight amount, if desired.

To demonstrate the effectiveness of skin preparations made in accordance with the present invention, tests were conducted to study (1) the water content of the stratum corneum and (2) the viscoelastic properties of skin before and after treatment.

EXAMPLE I

In an attempt to measure stratum corneum water content before and after treatment in accordance with the present invention, a skin surface hygrometer (manufactured by IBC Co. Japan) was employed. The water content was assessed from separate measurements of skin conductance and capacitance.

Tests were conducted to compare skin preparations containing both phosphatidylcholine (PC) and $C_{10}$–$C_{30}$ carboxylic acid sterol acid (SE) with preparations containing only PC or SE, and with a "control" preparation containing neither PC or SE. The control preparation was straight Miglyol 812 neutral oil, as previously described. The PC composition contained about 0.30 weight percent soy phosphatide NC-95, supplied by the American Lecithin Company, containing about 90 percent phosphatidylcholine (i.e. about 0.27 weight percent active phosphatidylcholine) in the neutral oil. The SE composition contained about 0.17 weight percent Super Sterol Ester, as previously described, in the neutral oil. The PC-SE composition, in accordance with the present invention, contained both the PC and the SE in the above weight percents. This is approximately an equimolar solution of the PC and SE, each being present at about $3.5 \times 10^{-4}$ molar concentration.

In 12 normal subjects (all female, aged 18 to 45 years) both skin conductance and capacitance were increased when subjects were treated with the above-described PC-SE composition, in accordance with the present invention twice a day for 24 days. For comparison, the subjects were also treated with the PC, SE and control compositions as well. In such cases, the difference in water content of stratum corneum before and after treatment was found to be statistically insignificant. (Table 1)

TABLE 1
VALUES OF SKIN HYDRATION AT VARIOUS BODY SITES
Normal Skin (12 subjects)

| | Initial | Day 7 | Day 14 |
|---|---|---|---|
| 1. Conductance (μmho) | | | |
| *(Face)* | | | |
| PC-SE | 20.1 ± 11.2 | 22.3 ± 11.7 | 22.9 ± 10.4 |
| PC | 20.1 ± 11.2 | 20.9 ± 12.2 | 20.8 ± 12.1 |
| SE | 20.1 ± 11.2 | 19.5 ± 13.3 | 20.2 ± 11.0 |
| control | 20.1 ± 11.2 | 19.8 ± 12.9 | 19.9 ± 12.5 |
| *(Upper Arm)* | | | |
| PC-SE | 10.4 ± 3.5 | 12.9 ± 3.1 | 13.2 ± 3.7 |
| PC | 10.4 ± 3.5 | 11.6 ± 7.9 | 11.9 ± 6.3 |
| SE | 10.4 ± 3.5 | 9.9 ± 3.3 | 10.3 ± 4.2 |
| control | 10.4 ± 3.5 | 9.7 ± 2.6 | 9.9 ± 2.8 |
| *(Forearm)* | | | |
| PC-SE | 15.8 ± 5.3 | 17.9 ± 6.1 | 18.5 ± 6.2 |
| PC | 15.0 ± 5.3 | 16.0 ± 6.8 | 17.1 ± 6.8 |
| SE | 15.0 ± 5.3 | 15.5 ± 6.1 | 15.9 ± 5.5 |
| control | 15.0 ± 5.3 | 14.6 ± 3.7 | 14.9 ± 4.1 |
| 2. Capacitance (pF) | | | |
| *(Face)* | | | |
| PC-SE | 3.2 ± 1.7 | 3.8 ± 1.6 | 4.2 ± 1.3 |
| PC | 3.2 ± 1.7 | 3.1 ± 1.8 | 3.2 ± 1.9 |
| SE | 3.2 ± 1.7 | 3.1 ± 1.5 | 3.1 ± 1.3 |
| control | 3.2 ± 1.7 | 3.1 ± 1.8 | 3.1 ± 1.5 |
| *(Upper Arm)* | | | |
| PC-SE | 1.9 ± 0.6 | 2.2 ± 0.9 | 2.6 ± 0.8 |
| PC | 1.9 ± 0.6 | 1.9 ± 0.5 | 1.9 ± 0.4 |
| SE | 1.9 ± 0.6 | 1.9 ± 0.3 | 1.9 ± 0.4 |
| control | 1.9 ± 0.6 | 1.8 ± 0.6 | 1.9 ± 0.7 |
| *(Forearm)* | | | |
| PC-SE | 2.7 ± 0.7 | 3.6 ± 0.9 | 3.7 ± 0.6 |
| PC | 2.7 ± 0.7 | 2.8 ± 0.7 | 3.2 ± 0.7 |
| SE | 2.7 ± 0.7 | 2.7 ± 0.6 | 2.7 ± 0.7 |
| control | 2.7 ± 0.7 | 2.6 ± 0.7 | 2.7 ± 0.6 |

In another test, 12 subjects who had severely dry skin condition (all female, aged 20 to 44 years) were treated with the above-identified skin preparations. The PC-SE composition produced a significant increase in skin water content, indicated by an increase in both skin conductance and capacitance values in all 12 subjects, even after only 7 days treatment. Although phosphatidylcholine or sterol ester alone produced slight increases in skin water content, the increase was statistically insignificant in 7 days of treatment. After 14 days, treatment with phosphatidylcholine alone did produce a measurable increase in skin water content, but only to a slight degree (Table 2).

TABLE 2
Severe Dry Skin (12 subjects)

| | Initial | Day 7 | Day 14 |
|---|---|---|---|
| 1. Conductance (μmho) | | | |
| *(Face)* | | | |
| PC-SE | 11.7 ± 4.6 | 16.8 ± 5.3 | 18.8 ± 6.7 |
| PC | 11.7 ± 4.6 | 12.7 ± 6.6 | 14.3 ± 5.1 |
| SE | 11.7 ± 4.6 | 12.3 ± 5.9 | 12.8 ± 6.8 |
| control | 11.7 ± 4.6 | 12.0 ± 5.1 | 11.9 ± 5.8 |
| *(Upper Arm)* | | | |
| PC-SE | 8.1 ± 2.7 | 9.8 ± 2.2 | 10.1 ± 3.1 |
| PC | 8.1 ± 2.7 | 8.5 ± 2.5 | 9.3 ± 2.7 |
| SE | 8.1 ± 2.7 | 8.3 ± 2.4 | 8.8 ± 3.0 |
| control | 8.1 ± 2.7 | 8.2 ± 3.0 | 8.7 ± 2.7 |
| *(Forearm)* | | | |
| PC-SE | 9.8 ± 3.9 | 12.5 ± 4.1 | 14.4 ± 4.5 |
| PC | 9.8 ± 3.9 | 10.0 ± 4.2 | 11.6 ± 4.0 |
| SE | 9.8 ± 3.9 | 9.9 ± 3.8 | 9.9 ± 2.9 |
| control | 9.8 ± 3.9 | 10.1 ± 4.4 | 10.3 ± 3.9 |
| 2. Capacitance (pF) | | | |
| *(Face)* | | | |
| PC-SE | 2.3 ± 1.1 | 2.9 ± 1.1 | 3.1 ± 1.3 |

TABLE 2-continued

| | Severe Dry Skin (12 subjects) | | |
|---|---|---|---|
| | Initial | Day 7 | Day 14 |
| PC | 2.3 ± 1.1 | 2.5 ± 1.8 | 2.8 ± 1.3 |
| SE | 2.3 ± 1.1 | 2.4 ± 1.6 | 2.5 ± 1.6 |
| control | 2.3 ± 1.1 | 2.4 ± 1.3 | 2.4 ± 1.2 |
| (Upper Arm) | | | |
| PC-SE | 1.6 ± 0.7 | 1.9 ± 0.5 | 2.1 ± 0.7 |
| PC | 1.6 ± 0.7 | 1.7 ± 0.8 | 1.9 ± 0.6 |
| SE | 1.6 ± 0.7 | 1.7 ± 0.7 | 1.7 ± 0.6 |
| control | 1.6 ± 0.7 | 1.7 ± 0.9 | 1.7 ± 0.7 |
| (Forearm) | | | |
| PC-SE | 1.3 ± 0.6 | 1.9 ± 0.7 | 2.4 ± 1.1 |
| PC | 1.3 ± 0.6 | 1.5 ± 0.9 | 1.7 ± 0.8 |
| SE | 1.3 ± 0.6 | 1.4 ± 0.6 | 1.4 ± 0.8 |
| control | 1.3 ± 0.6 | 1.4 ± 0.8 | 1.5 ± 1.0 |

EXAMPLE II

To study the effects of the skin preparation of the present invention on the viscoelastic properties of the skin, tests were conducted by using a suction device to measure skin flexibility. In this study, a suction device was used to measure the flexibility of the skin of the face, upper arm, and forearm of 12 normal female subjects and 12 female subjects diagnosed as having severe dry skin conditions. The ability of topically applied test substances to influence the viscoelastic properties of the skin over a 14 day period was determined. Measurements of the changes in the hysteresis loop were taken as an index of the effectiveness of the test substances. Table 3 shows the results for the normal skin subjects and Table 4 for the dry skin subjects.

TABLE III

NORMAL SKIN (12 SUBJECTS)
Percent viscoelasticity Increase After Treatment

| | After 7 Days | After 14 Days |
|---|---|---|
| PC-SE | 22 | 30 |
| PC | 10 | 12 |
| SE | 7 | 9 |
| Control | 6 | 8 |

TABLE IV

SEVERE DRY SKIN (12 SUBJECTS)
Percent Viscoelasticity Increase After Treatment

| | After 7 Days | After 14 Days |
|---|---|---|
| PC-SE | 53 | 65 |
| PC | 21 | 26 |
| SE | 15 | 20 |
| Control | 12 | 17 |

The results indicate that the combination of phosphatidylcholine and $C_{10-30}$ carboxylic acid sterol ester significantly increases skin flexibility both in normal subjects and in those with with severely dry skin. They also indicate that the complex of phosphatidylcholine and $C_{10-30}$ carboxylic acid sterol ester is much more effective than either component alone for increasing skin flexibility.

EXAMPLE III

Based on the present invention, the following three skin preparations (Formulation A—cream, Formulation B—lotion, and Formulation C—facial cream) were prepared. Variations and modifications can, of course, be made without departing from the spirit and scope of this invention. All formulations are presented in percent by weight.

| | Formulation (wt. %) | | |
|---|---|---|---|
| Ingredient | A (CREAM) | B (LOTION) | C (FACIAL CREAM) |
| Phosphatide* | 0.30 | 0.30 | 0.10 |
| C10-30 Carboxylic acid sterol ester | 0.17 | 0.17 | 0.06 |
| Caprylic/capric triglyceride | 2.00 | 3.00 | 3.50 |
| Squalane | 4.00 | 1.00 | 2.50 |
| Mineral Oil | 8.00 | — | — |
| Propylene glycol | — | — | 1.50 |
| Glycerin 96 X USP | 6.00 | 3.00 | 2.50 |
| Stearic acid | 1.00 | 0.50 | 0.50 |
| Glycol stearate | 1.00 | 0.50 | 0.50 |
| Glyceryl stearate | 1.00 | 2.00 | 1.50 |
| Dimethicone | 1.50 | 1.00 | 0.50 |
| PEG-50 Stearate | 1.00 | 1.00 | 1.00 |
| Myristyl myristate | 0.50 | 0.50 | 0.50 |
| Cetyl alcohol | 0.50 | 0.50 | 0.50 |
| Magnesium aluminum silicate | 0.20 | 0.05 | 0.20 |
| Carbomer 934 | 0.20 | 0.10 | 0.20 |
| EDTA tetrasodium tetrahydrate | 0.03 | 0.03 | 0.03 |
| Sodium hydroxide | 0.07 | 0.05 | 0.07 |
| Butylated hydroxytoluene | 0.03 | 0.03 | 0.03 |
| Preservative (Diazolidinyl Urea) | 0.25 | 0.15 | 0.15 |
| Purified water USP | 72.25 | 86.12 | 84.16 |

*Phosphatide was supplied by American Lecithin Company (Soy Phosphatide NC-95 containing 90% of phosphatidylcholine).

The skin moisturizing action of the above three formulations was evaluated. In these evaluations, twenty four (24) female subjects (age from 18 to 52, average 39 years old) were used. Prior to testing, the panelists were asked to wash their forearms with a mild detergent, (Ivory soap), rinse with warm water for 2 minutes, and pat dry. The washing procedure was followed by a 60 minute equilibration period in a room that was maintained at constant humidity (45% relative humidity) and temperature (20° C.). This period allowed the panelists to adjust to the conditions of the testing environment. One site was delineated on each forearm, and the rate of water loss was determined at each site. After the measurements were taken, one of the sites was treated with 0.05 ml of two different test products on a 4×4 cm square area each. The water loss measurement were repeated on both sites at 60, 120, 180, 240, and 300 minutes post-treatment using a Servo Med. Dual Probe Evaporimeter. It was found that these compositions were capable of prolonged and balanced moisturing action over at least 5 hours, providing a layer of protection at the stratum corneum of the skin and immediately adjoining layers.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A moisturizing skin preparation comprising a combination of about 0.05 to about 5 percent by weight of a skin compatible phosphatide, about 0.02 to about 5 percent by weight of one or more $C_{10}$-$C_{30}$ carboxylic acid sterol esters and about 0.5 to about 10 percent by weight of at least one $C_6$-$C_{12}$ alkanoic triglyceride in a dermatologically acceptable carrier.

2. The preparation of claim 1 wherein the phosphatide comprises phosphatidylcholine.

3. The preparation of claim 2 wherein the phosphatide is in soy lecithin containing at least about 5 percent by weight phosphatidylcholine.

4. The preparation of claim 3 wherein the soy lecithin contains at least 90 percent by weight phosphatidylcholine.

5. The preparation of claim 1 comprising about 1 to 3 parts by weight of the sterol ester for each 3 parts by weight of phosphatide.

6. The preparation of claim 5 comprising about 2 parts by weight of sterol ester for each 3 parts by weight of phosphatide.

7. The preparation of claim 5 comprising approximately equimolar amounts of sterol ester and phosphatide.

8. The preparation of claim 4 comprising about 0.1 to about 1 percent by weight phosphatide.

9. The preparation of claim 8 comprising about 0.05 to 1 percent by weight sterol ester.

10. The preparation of claim 9 wherein the alkanoic triglyceride is a mixed acid triglyceride comprising about 50 to about 65 percent by weight caprylic acid triglyceride and about 30 to about 45 percent by weight capric triglyceride.

11. The preparation of claim 10 comprising about 2 to about 4 percent by weight of the alkanoic triglyceride.

12. The preparation of claim 1 comprising about 0.05 to about 1 percent by weight of sterol ester.

13. The preparation of claim 12 comprising about 2 to about 4 percent by weight of the alkanoic triglyceride.

14. The preparation of claim 1 wherein the alkanoic triglyceride is a mixed acid triglyceride comprising about 50 to about 65 percent by weight caprylic acid triglyceride and about 30 to about 45 percent by weight capric triglyceride.

15. The preparation of claim 1 in the form of a skin cream, face cream, lotion or ointment.

16. A method of treating dry skin comprising topically applying a moisturing skin preparation as described in claim 1.

* * * * *

UNITED STATES PATENT AND TRADEMARK OFFICE
CERTIFICATE OF CORRECTION

PATENT NO. : 4,760,096
DATED : July 26, 1988
INVENTOR(S) : Sakai, Kirk et al.

It is certified that error appears in the above-identified patent and that said Letters Patent are hereby corrected as shown below:

On the cover page of the patent, change " [73] Assignee: Schering Corporation, Kenilworth, N.J." to: -- [73] Assignee: Key Pharmaceuticals Inc., Miami, Fla. --

Signed and Sealed this

Tenth Day of January, 1989

Attest:

DONALD J. QUIGG

Attesting Officer

Commissioner of Patents and Trademarks